(12) United States Patent
Morrow

(10) Patent No.: US 7,963,934 B2
(45) Date of Patent: Jun. 21, 2011

(54) TAMPON APPLICATOR ASSEMBLY

(76) Inventor: Jacqueline M. Morrow, Fredericksburg, VA (US)

( * ) Notice: Subject to any disclaimer, the term of this patent is extended or adjusted under 35 U.S.C. 154(b) by 575 days.

(21) Appl. No.: 12/076,110

(22) Filed: Mar. 13, 2008

(65) Prior Publication Data
US 2009/0112148 A1 Apr. 30, 2009

Related U.S. Application Data

(60) Provisional application No. 61/000,361, filed on Oct. 25, 2007.

(51) Int. Cl.
*A61F 13/20* (2006.01)

(52) U.S. Cl. ............. 604/11; 604/12; 604/13; 604/14; 604/15; 604/16; 604/17; 604/18; 604/904; 206/438; 206/439; 206/440

(58) Field of Classification Search ............. 604/11–18, 604/904; 206/438–440
See application file for complete search history.

(56) References Cited

U.S. PATENT DOCUMENTS

| | | | |
|---|---|---|---|
| 3,884,233 A * | 5/1975 | Summey | 604/15 |
| 4,312,348 A * | 1/1982 | Friese | 604/363 |
| 4,421,504 A * | 12/1983 | Kline | 604/12 |
| 4,690,671 A * | 9/1987 | Coleman et al. | 604/12 |
| 5,616,337 A | 4/1997 | Kasianovitz et al. | |
| 5,676,647 A * | 10/1997 | Cimber | 604/11 |
| 5,730,294 A * | 3/1998 | Blosser et al. | 206/581 |
| 5,738,646 A | 4/1998 | Fox et al. | |
| 5,782,793 A | 7/1998 | Nielson | |
| 5,792,096 A | 8/1998 | Rentmeester et al. | |
| 5,800,377 A | 9/1998 | Campion et al. | |
| 5,891,081 A | 4/1999 | McNelis et al. | |
| 5,988,386 A * | 11/1999 | Morrow | 206/581 |
| 6,592,540 B2 * | 7/2003 | DeCarlo | 604/12 |
| 7,314,135 B1 * | 1/2008 | Drotar | 206/459.1 |
| D564,363 S * | 3/2008 | Rhea | D9/734 |
| 7,708,726 B2 * | 5/2010 | Hayes et al. | 604/385.17 |
| 2004/0112769 A1 * | 6/2004 | Perry | 206/219 |
| 2006/0213919 A1 * | 9/2006 | Heuer et al. | 221/33 |

OTHER PUBLICATIONS

Definitions of "rigid", "container", "lid", "vessel" and capsule, Websters Third New International Dictionary,unabridged, 1993.*
Definition of "container", Merriam-Webster OnLine.*

* cited by examiner

Primary Examiner — Tatyana Zalukaeva
Assistant Examiner — Ginger T Chapman
(74) Attorney, Agent, or Firm — Richard C. Litman

(57) ABSTRACT

The tampon applicator assembly includes a tampon applicator section, an outer housing section, and a plunger section. The combined tampon applicator section and plunger section function as a conventional plunger-type tampon applicator. The outer housing section includes a sleeve with a proximal portion and a distal portion. The (distal) insertion end of the tampon applicator section essentially fits inside the proximal portion of the sleeve, and the distal portion of the sleeve is designed to accommodate a feminine hygiene product, such as a pad, a disposable wipe, a towelette disposal mitt, a simple disposal bag, and other products associated with menstruation.

16 Claims, 6 Drawing Sheets

TAMPON APPLICATOR ASSEMBLY

CROSS-REFERENCE TO RELATED APPLICATIONS

This application claims the benefit of U.S. Provisional Patent Application Ser. No. 61/000,361, filed Oct. 25, 2007.

BACKGROUND OF THE INVENTION

1. Field of the Invention

The present invention relates to feminine hygiene products, and particularly to a tampon applicator assembly that includes a tampon and associated feminine hygiene products.

2. Description of the Related Art

Although a woman's menstrual cycle occurs at approximately the same time each month, the actual menstrual flow may begin unexpectedly. Consequently many women always carry a feminine hygiene product (i.e. a tampons, sanitary napkins, panty liners, etc.) in their purse, in their coat pocket, or in other quickly accessible locations. However, when a feminine hygiene product is stored in a purse (for example) for any length of time, the outer paper wrapping often tears and the product may become contaminated or damaged. Using feminine hygiene products that are damaged or contaminated may result in illness or injury. Specifically, using a contaminated tampon may cause infection and using a damaged applicator can result in pain and discomfort during insertion.

This problem is multiplied when a woman carries a combination of products. Women frequently use a protective pad (such as a panty liner) in combination with a tampon as a means of preventing the unwanted and embarrassing leakage of menstrual fluids. They may also carry other products in combination with a tampon such as disposable wipes, pads, a pharmaceutical, a towelette disposal mitt, and the like. The use of a combination of products may be particularly important during the early stages of the menstrual period.

The prior art that is most applicable to the current invention is the inventor's previously issued patent (U.S. Pat. No. 5,988,386). An embodiment of the inventor's previous US patent discloses a tampon applicator that incorporates a storage compartment within the tampon plunger area. However, the inventor's previous invention is structurally distinguishable from the current invention and, as a practical matter, it is questionable whether the tampon plunger compartment of the inventor's previous patent provides sufficient space to accommodate some types of feminine hygiene products.

Further, many currently available tampons have reduced diameter plungers so that any compartment within the plunger would be extremely small. Examples of these types of tampons include the Gentle Glide® tampon marketed by Playtex Products, Inc. of Westport, Conn. and the Pearl and Sport tampons marketed by Tampax, Inc. of Denver, Colo. Additionally, tampons with no conventional applicator (and therefore no plunger section) are also commonly available in the market place.

The need exists for a tampon applicator assembly that is compatible with tampons that have reduced diameter plungers and have sufficient space to store at least one feminine hygiene product (as defined in this specification) in combination with a tampon. It would be desirable that the tampon applicator assembly can be stored and carried in a woman's purse without damaging and contaminating the feminine hygiene products within the tampon applicator assembly.

Thus, a tampon applicator assembly solving the aforementioned problems is desired.

SUMMARY OF THE INVENTION

The tampon applicator assembly includes at least a tampon applicator section and an outer housing section. The tampon applicator section may include a tampon encompassed by a tampon casing. A finger grip portion extends from the proximal end of the tampon casing. The outer housing section is coaxial with the tampon applicator section and comprises a rigid sleeve with a distal portion and a proximal portion. The sleeve proximal portion encompasses at least the insertion end of the tampon casing. At least one feminine hygiene product is contained in the distal portion of the sleeve. The tampon applicator assembly is designed so that the proximal portion of the sleeve protects the insertion end of the tampon casing, and the distal portion of the sleeve protects the feminine hygiene product. Consequently the feminine hygiene product, the insertion end of the tampon casing, and the tampon remain uncontaminated prior to use.

The tampon applicator assembly need not include a tampon (insertion) casing. In this event, the tampon applicator assembly includes a tampon disposed in a proximal compartment of a rigid sleeve, and a feminine hygiene product disposed in the distal compartment of the rigid sleeve. The distal compartment has a larger diameter than the proximal compartment. The rigid sleeve encompasses the tampon and the feminine hygiene product so that the tampon and the feminine hygiene product are protected from contamination prior to use.

The tampon applicator assembly may provide a user with a disposal mitt. In this event, the tampon applicator assembly includes a tampon outer casing that encompasses a tampon, and a sleeve with a proximal portion that at least partially encompasses the insertion end of the tampon casing. A towelette disposal mitt is contained in the distal portion of the sleeve. The towelette disposal mitt is adapted to be used during insertion and removal of the tampon so that a user has an enhanced ability to clean the affected areas. The towelette disposal mitt can also be turned inside out and used as a soiled tampon disposal bag after the tampon has been removed.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
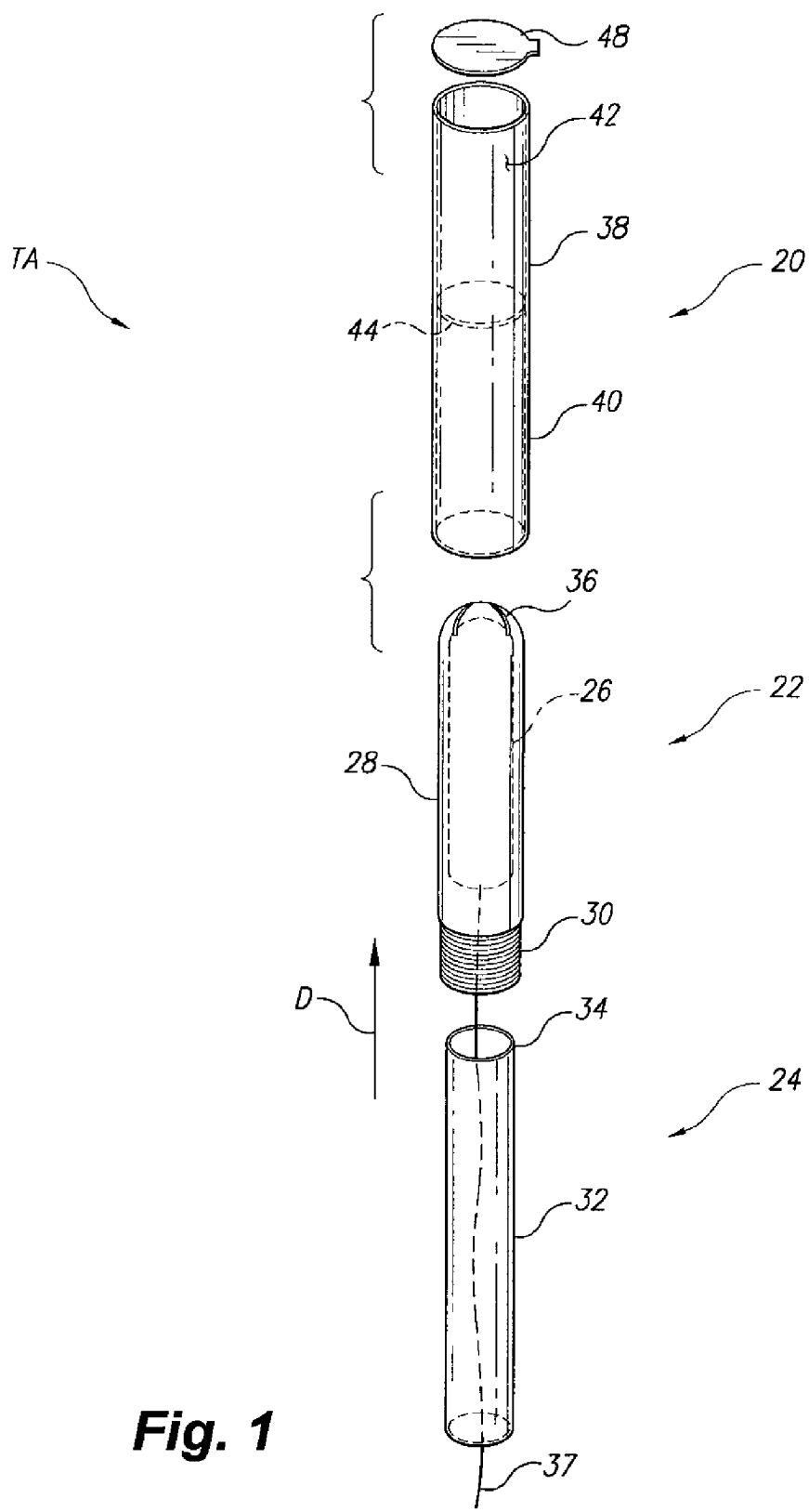
FIG. 1 is an exploded perspective view of a tampon applicator assembly according to the present invention.

The present invention is directed to a tampon applicator assembly TA. As best shown in FIG. 1, the tampon applicator assembly TA includes an outer housing section 20, a tampon applicator section 22, and a plunger section 24. In the preferred embodiment, the outer components of the tampon applicator assembly TA are comprised of rigid or semi-rigid cardboard, plastic, or coated materials. In further embodiments, the components of the tampon applicator assembly may be comprised of any materials suitable for the function of the associated component.

The combination of the applicator section 22 and the plunger section 24 are well known in the art and comprise a conventional tampon applicator. The tampon applicator section 22 includes a tampon 26 that is encompassed and at least partially enveloped by a tampon casing 28. Knurled finger grips 30 may extend from the proximal end of the tampon casing 28 so that a user can conveniently hold the tampon casing 28 in place during the tampon insertion process. The plunger section 24 generally comprises a cylindrical plunger mechanism 32. The distal end 34 of the plunger mechanism 32 extends into the tampon casing 28 and rests adjacent to the tampon 26 in the packaged configuration prior to use. A tampon extraction string 37 extends from the tampon 26 through the plunger mechanism 32.

In operation, a tampon 26 is conventionally inserted by placing the (distal) insertion end 36 of the tampon casing 28 within the user's vaginal opening and applying pressure to the plunger mechanism 32 so that the plunger mechanism 32 advances in the direction D and the tampon 26 is expelled from the insertion end 36 of the tampon casing 28 and into the user's vaginal cavity. Although FIG. 1 depicts the tampon casing 28 as having a "petal" type opening, the tampon casing 28 may have any opening known in the art. The tampon 26 may be subsequently removed by grasping and pulling the extraction string 37 so that the tampon 26 is extracted from the vaginal cavity.

As best shown in FIG. 1, the tampon applicator assembly TA of the current invention further comprises an outer housing section 20. The outer housing section 20 comprises a sleeve 38 with at least a proximal 40 and a distal 42 portion. In the preferred embodiment the sleeve 38 is a rigid, unobstructed, open-ended tube. In alternative embodiments the proximal 40 and distal 42 portions of the sleeve may be divided by one or more partitions 44. In a further embodiment a single rigid partition that is integral with the sleeve may divide the interior of the sleeve 38 into a proximal compartment 40 and a distal compartment 42.

As best shown in FIG. 1, the distal portion 42 of the sleeve 38 is generally hollow and may be hermetically sealed by a removable upper closure device 48. In the preferred embodiment the upper closure device 48 is a disposable lid comprised of plastic, paper, cardboard, foil or the like. Alternatively, the closure device 48 may be designed to be re-attachable so that the outer housing section 20 is re-usable. Examples of re-attachable closure devices include a screw-type mechanism, and a snap-on cap, or the like. The closure device 48 may be moisture and contamination resistant so that the contents of the distal portion 42 of the sleeve 38 are not damaged or otherwise compromised.

Figures 2, 3:
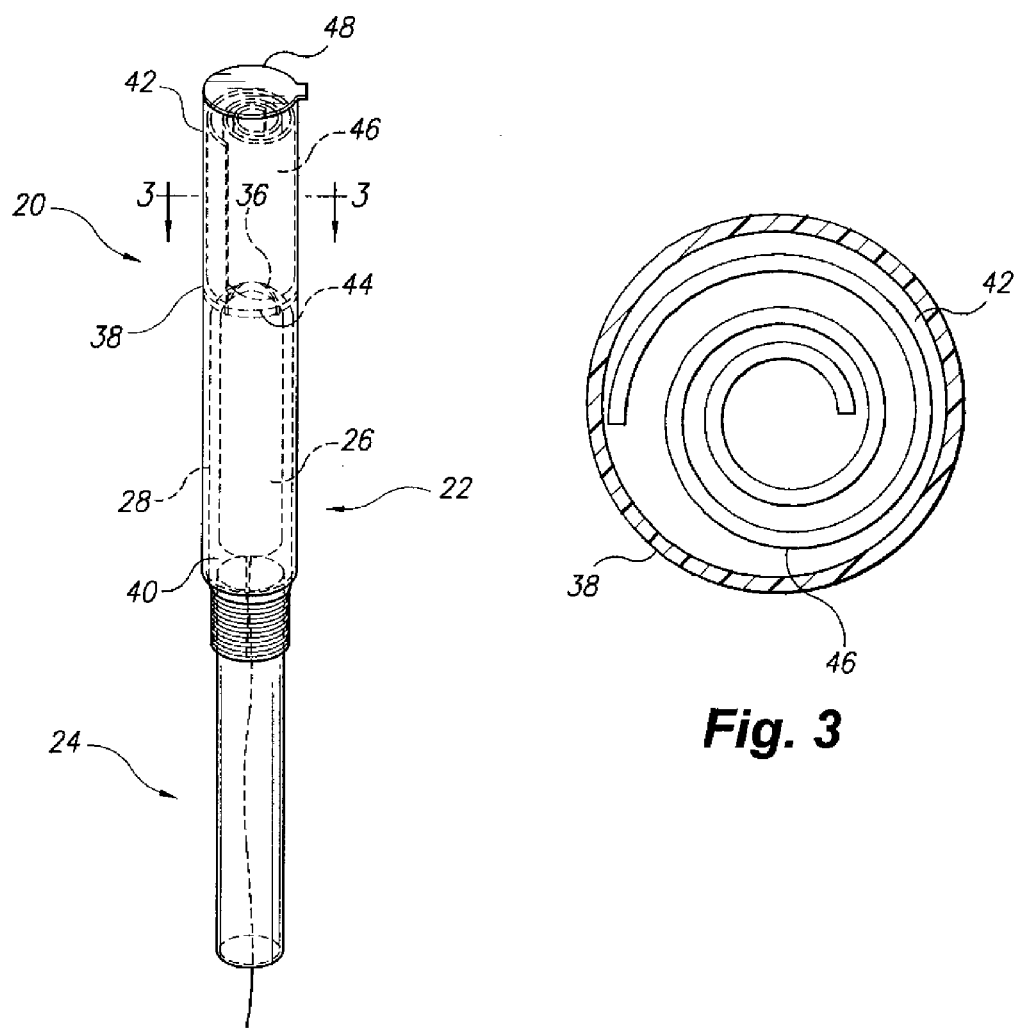
FIG. 2 is a perspective view of a tampon applicator assembly according to the present invention in an assembled pre-use configuration.
FIG. 3 is a sectional view taken along the lines 3-3 of FIG. 2.

As best shown in FIG. 2, in the packaged pre-use position, the (distal) insertion end 36 of the tampon casing 28 extends into the proximal portion 40 of the sleeve 38 so that the proximal portion 40 envelops the entire tampon casing 28 except the knurled finger grip portion 30. This configuration protects the tampon applicator section 22 generally, and specifically prevents the contamination of the insertion end 36 of the tampon casing 28 and ultimately the tampon 26. In an alternative embodiment, the tampon 26 alone (without the tampon casing 28 and plunger section 24) may be enclosed within the proximal portion 40 of the sleeve 38.

Figure 8:
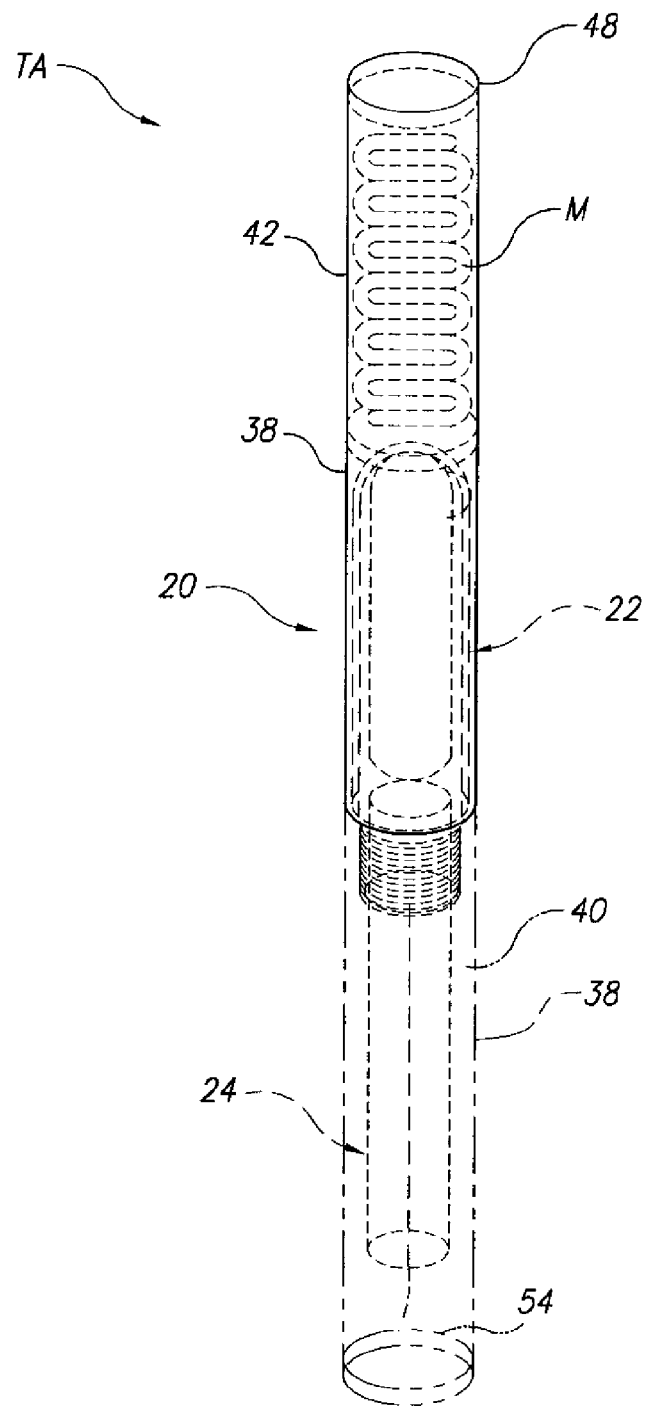
FIG. 8 is a perspective view of another alternative embodiment of a tampon applicator assembly according to the present invention in which the proximal portion of the outer housing section sleeve is enlarged to completely envelope the tampon applicator and plunger sections.

As shown in FIGS. 2, 3, and 8, the distal portion 42 of the sleeve 38 may contain various feminine hygiene products. Specifically, FIGS. 2 and 3 show a disposable wipe 46 rolled and stored in the distal portion 42 of the sleeve 38. FIG. 8 shows a towelette disposal mitt M that is also stored in the distal portion 42 of the sleeve 38. The distal portion 42 of the sleeve 38 may also contain other feminine hygiene products either alone or in various combinations.

For the purpose of this application, a "feminine hygiene product" may be defined as at least one of the following: a towelette disposal bag/mitt, a disposable wipe, a panty liner, a sanitary napkin, an extra tampon, an absorbent pad, a moistened towelette, a disposal bag, a pharmaceutical, a medicinal or non-medicinal lotion, a lubricant, a cleanser, a spermicidal agent, an anti-fungal agent, or any other generally medicinal or hygienic product known in the art.

In alternative embodiments, the proximal portion 40 of the sleeve 38 may also contain at least one feminine hygiene product. For example, the distal portion 42 of the sleeve 38 may contain a wipe and the proximal portion 40 of the sleeve 38 may contain a pad so that there is no tampon applicator section 22 or plunger section 20.

In a further embodiment, the subject matter of the current invention may be combined with the subject matter of the inventor's previous US patent (U.S. Pat. No. 5,998,386). In this embodiment, at least one feminine hygiene product may be stored in the distal portion 42 of the sleeve 38, a tampon 26 and applicator 28 are stored in the proximal portion 40 of the sleeve 38, and an additional feminine hygiene product is stored in the tampon applicator plunger compartment, as disclosed in the inventor's previous patent, which is hereby incorporated by reference.

Figure 4:
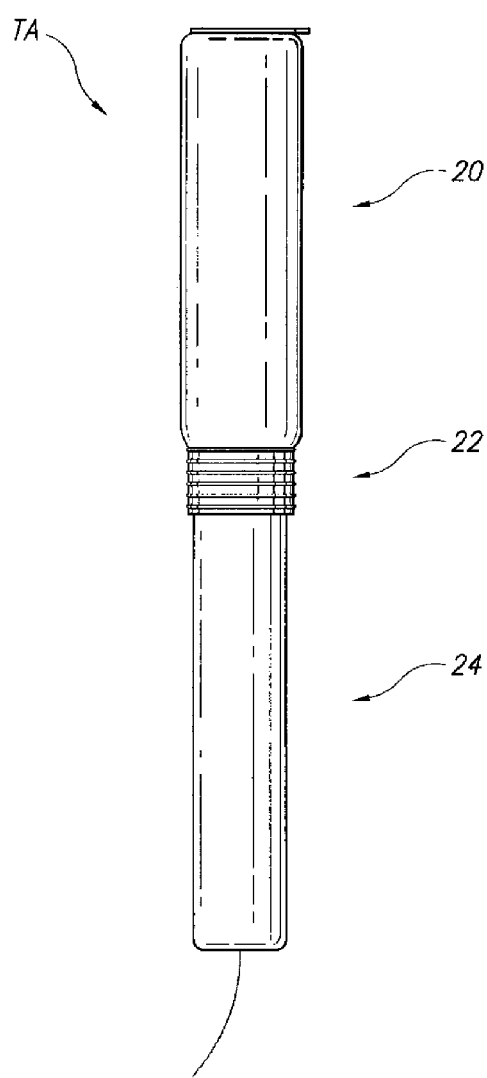
FIG. 4 is a front view of a tampon applicator assembly according to the present invention in an assembled pre-use configuration.

FIG. 4 shows an exterior profile view of the tampon applicator assembly TA of FIGS. 1-3 in the assembled configuration prior to use. In the preferred embodiment the entire assembly is shrink-wrapped in plastic so that the plunger section 24 is held in connection with the tampon applicator section 22 and outer housing section 20. Alternatively the plunger section 24, tampon section 22, and outer housing section 20 may be simply conventionally packaged in plastic, paper, or foil. The tampon applicator assembly TA sections 20, 22, 24 may also be internally and/or externally joined with a frictional interference fit. In a further embodiment the sections 20, 22, 24 may be joined with a transparent or an otherwise colored tape-type material or an adhesive.

Figure 5:
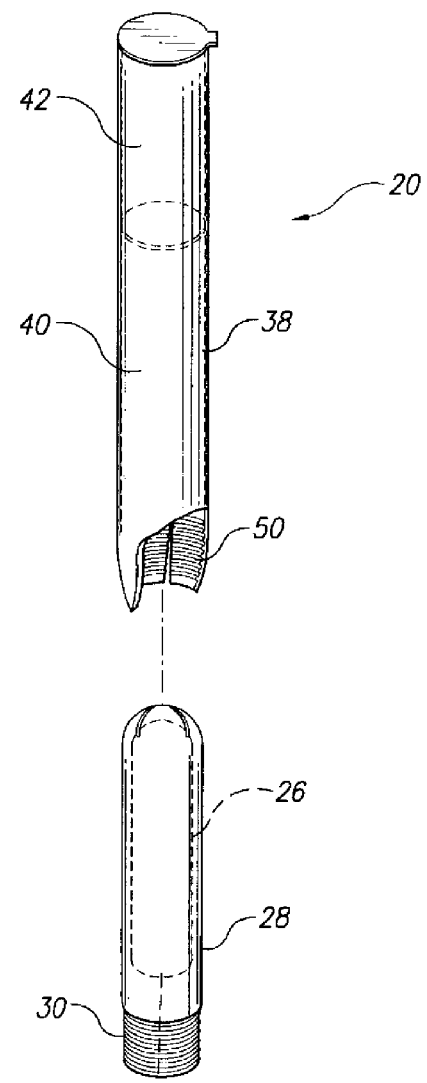
FIG. 5 is a partially exploded perspective view of an alternative embodiment of a tampon applicator assembly according to the present invention with threading/texturing on the interior of the proximal end of the outer housing section sleeve.
Figure 6:
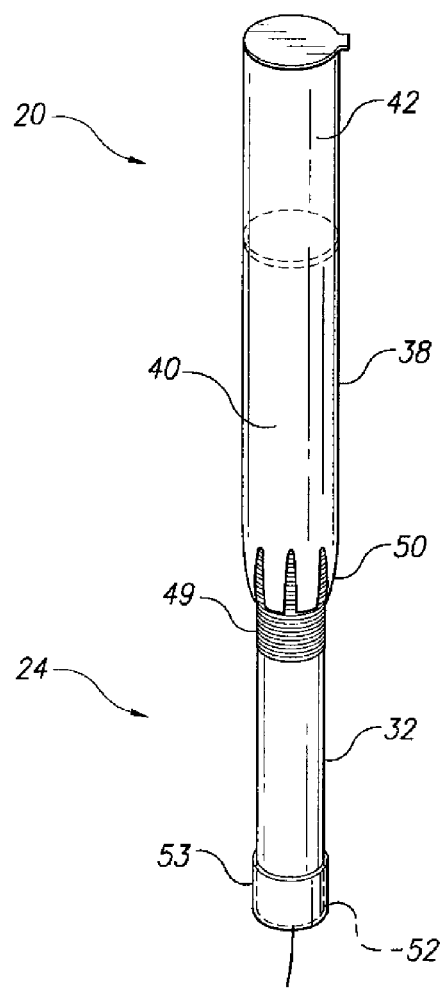
FIG. 6 is an assembled perspective view of the tampon applicator assembly of FIG. 5, which also includes the plunger section.

As best shown in FIG. 5, in an additional embodiment the proximal end 50 of the sleeve 38 of the outer housing section 20 may be knurled, threaded, corrugated, serrated, or otherwise textured or modified. This texturing or modification is designed to mesh with the corresponding texturing/threading modification on the finger grip portion 30 of the tampon casing 28 so that the tampon casing 28 and the sleeve 38 fit together to form a secure connection, as best shown in FIG. 6. The proximal end 50 of the sleeve 38 may be generally rounded to further streamline the packaging, as shown in FIG. 5.

As also shown in FIG. 6, the plunger mechanism 32 may have threading/texturing that corresponds with the internal (or alternatively external) surface of the finger grip portion 30 of the tampon casing 28 so that the plunger mechanism 32 is similarly securely adjoined to the finger grip portion 30. The opposite non-threaded/non-textured proximal end 52 of the plunger mechanism 32 could then be used during the tampon insertion process to urge the tampon 26 from the tampon casing 28. The proximal end 52 of plunger 32 may have a cap 53 that is removable prior to use so that the proximal end 52 of the plunger 32 is protected from contamination. Further, the diameter of the non-threaded portion of the plunger 32 may be reduced to so that the reduced diameter of the plunger 32 sides easily into the finger grip portion 30 of the tampon casing 28 (best shown in FIG. 1) to eject the tampon 26 during the tampon insertion process.

As best shown in FIG. 5, in an alternative embodiment, the plunger section 24 may be omitted so that a user uses her finger in a manner similar to a plunger to force the tampon 26 from the tampon casing 28. In another embodiment, the plunger section 24, finger grip 30 and tampon casing 28, may all be omitted so that only the tampon 26 is stored in the proximal portion 40 of the sleeve 38. In this embodiment the user manually inserts the tampon 26 without the use of the other components.

Figure 7:
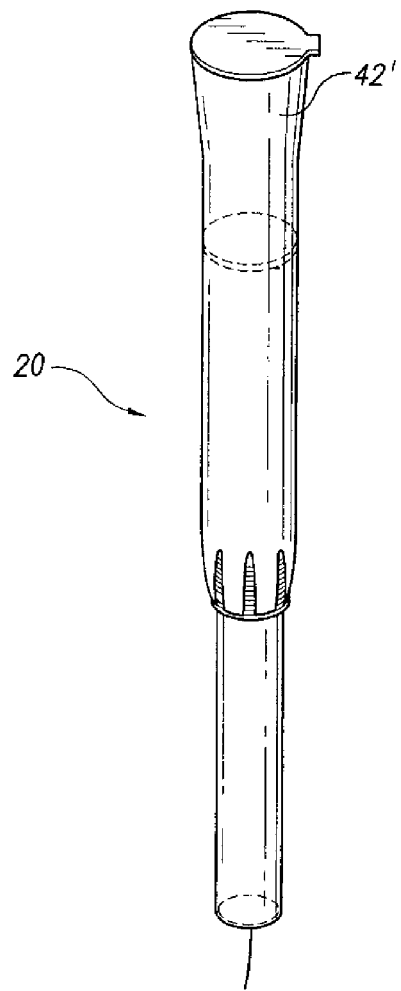
FIG. 7 is a perspective view of another alternative embodiment of a tampon applicator assembly according to the present invention in which the distal portion of the outer housing section sleeve is enlarged.

As best shown in FIG. 7, the size and shape of the distal portion 42 of the outer housing section 20 may be modified and enlarged to accommodate various feminine hygiene products. This is particularly important with regard to tampons with reduced diameter plungers. In FIG. 7, the distal portion 42 of the sleeve 38 has been modified and enlarged relative to the shape of the distal portion 42 in FIGS. 1-6. Specifically, the distal portion 42 of the sleeve 38 in FIG. 7 has a generally inverted frustoconical shape, however, in alternative embodiments, any shape should be considered within the scope of the invention.

As best shown in FIG. 8, in a further embodiment, the length of the sleeve 38 may be increased so that the sleeve 38 completely encompasses the tampon applicator section 22 and the plunger section 24. Specifically, in this embodiment, the tampon applicator section 22 and the plunger section 24 are positioned within the proximal portion 40 of the sleeve 38. In a further embodiment, the entire sleeve 38 may be comprised of a non-rigid material such as a foil, a plastic wrap, or the like.

The FIG. 8 embodiment includes a lower closure device 54 opposite the upper closure device 48 so that the contents of the proximal portion 40 may be removed. FIG. 8 shows that the distal portion 42 may include a towelette disposal mitt M. As discussed above, other hygiene and medicinal products should be considered within the scope of the invention as well.

Figure 9:
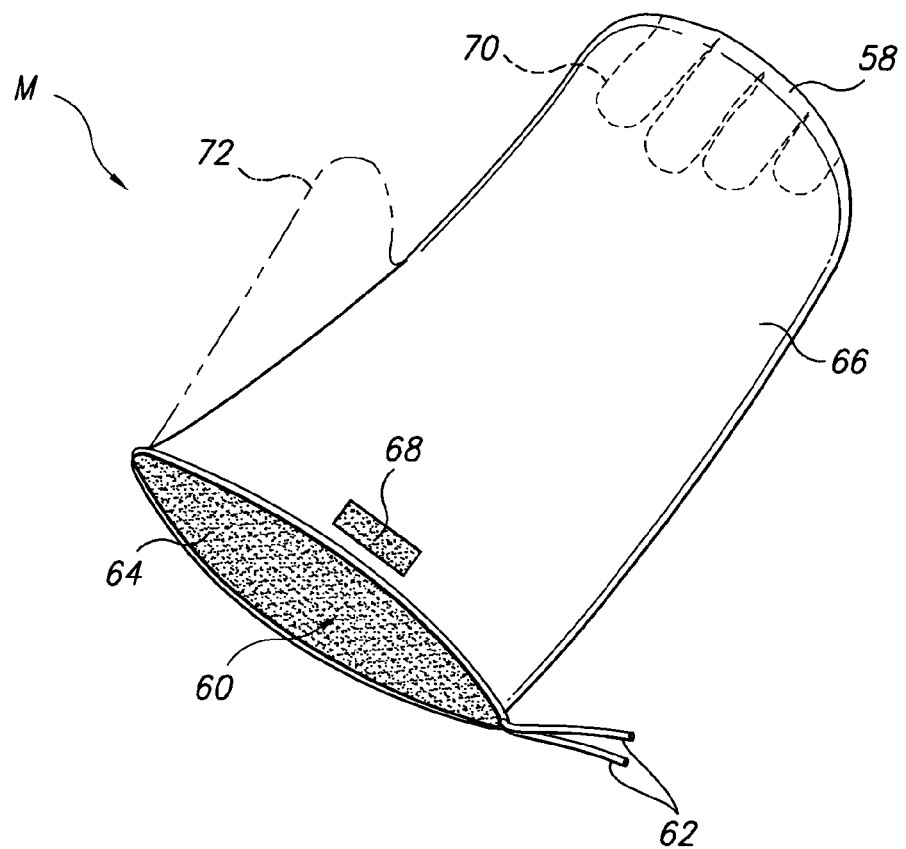
FIG. 9 is a perspective view of the towelette disposal mitt of a tampon applicator assembly according to the present invention, shown in the pre-use configuration.
Figure 10:
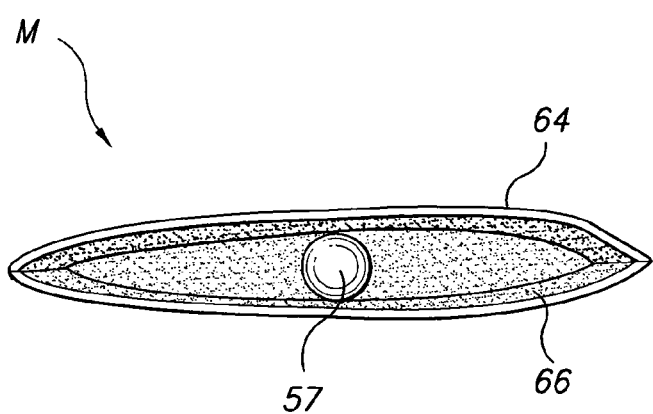
FIG. 10 is a top view of the towelette disposal mitt of FIG. 9 containing a soiled tampon in the post-use disposal bag configuration.

As best shown in FIGS. 8, 9, and 10, one of the products that may be enclosed in the distal portion 42 of the sleeve 38 is a towelette disposal mitt M. The purpose of the mitt M is to enable the user to cleanse herself and to protect her hand during the tampon insertion and removal process.

As best shown in FIG. 9, the mitt M has a closed end 58, and an opposite open end 60 that may be selectively closed. The open end 60 may have a variety of closing or sealing means, such as a drawstring 62, an incorporated twist-tie, or an adhesive strip. The open end 60 of the mitt M may also incorporate a sealing means comprising at least one flexible plastic tongue-and-groove fastener (commercially available under the trade name Ziploc®). There may be a sealing means on both the interior and exterior of the mitt M so that the seal can be used both before and after the mitt M is turned inside out. The sealing means preferably creates an airtight and watertight seal.

As best shown in FIG. 9, the interior 64 of the mitt M may be comprised of a non-permeable plastic liner to protect the hand of a user. The exterior 66 of the mitt M may be comprised of a towelette or a similar soft and/or absorbent material. The towelette surface 66 may be pre-moistened for the comfort of a user and to enhance the cleaning process. The mitt M may have a tubular configuration or it may include finger-type extensions 70 and/or a thumb extension 72.

As best shown in FIG. 9, the mitt M may include an attaching means 68 on the mitt's exterior 66. The attaching means 68 may be comprised of an adhesive strip, such as a releasable tape; a clip; a clamp; or a safety pin or the like. The attaching means 68 allows a user to temporarily attach the mitt M to her calf or thigh during the tampon insertion and removal process and thereby avoid the necessity of placing the mitt M on the restroom floor. In a further embodiment, the attaching means 68 may further include a magnetic attachment device, such as a magnetic disc or strip or the like, which allows the user to attach the mitt M to a metal partition commonly found in public restrooms.

The tampon extraction process is completed by grasping the soiled tampon 57 with the mitt M, and turning the mitt M inside out around the tampon 57. As best shown in FIG. 10, after the tampon is removed and the mitt M is turned inside out, the mitt M forms a disposal bag around the soiled tampon 57 so that the impermeable (previously) interior surface of the mitt 64 forms an outer shell to prevent the leakage of fluids associated with the soiled tampon 57.

The mitt M may be packaged completely independently of the tampon applicator assembly TA, or (as indicated above) it may be packaged within the distal portion of the sleeve 38. In the preferred embodiment the mitt M is opaque, for discreet disposal.

For the foregoing reasons the current invention provides a versatile tampon applicator assembly capable of preserving feminine hygiene products in an uncontaminated state until the user is ready to use the products. It is understood that the present invention is not limited to the embodiments described above, but encompasses any and all embodiments within the scope of the following claims.

I claim:

1. A tampon applicator assembly, comprising:
   a tampon applicator section having:
   a tampon;
   a tampon casing encompassing the tampon, the tampon casing having a distal insertion end and a proximal end; and
   a finger grip portion defining the proximal end of the tampon casing; and an outer housing section coaxial with the tampon applicator section, the outer housing section having:

a sleeve having a distal portion and a proximal portion, the proximal portion encompassing at least the insertion end of the tampon casing, wherein a partition separates the interior of the sleeve into distinct proximal and distal portions; and at least one feminine hygiene product, the feminine hygiene product being disposed in the distal portion of the sleeve;

wherein the partition protects the insertion end of the tampon casing and the distal portion of the sleeve protects the feminine hygiene product so that the feminine hygiene product, the insertion end of the tampon casing, and the tampon remain uncontaminated prior to use.

2. The tampon applicator assembly of claim 1, further comprising a plunger section coaxial with the outer housing section and the tampon applicator section, the plunger section having a plunger mechanism.

3. The tampon applicator assembly of claim 1, wherein the distal portion of the sleeve has a larger diameter than the proximal portion of the sleeve, and the proximal portion of the sleeve has a larger diameter than the tampon casing.

4. The tampon applicator assembly of claim 3, wherein the distal portion of the sleeve has a frustoconical shape.

5. The tampon applicator assembly of claim 1, wherein the proximal portion of the sleeve envelops the entire tampon casing except the finger grip portion.

6. The tampon applicator assembly of claim 5, wherein the finger grip portion is knurled.

7. The tampon applicator assembly of claim 5, wherein an interior of the proximal portion of the sleeve is one of textured and threaded to mesh with the finger grip portion of the tampon casing so that the sleeve is securely joined with the tampon casing.

8. The tampon applicator assembly of claim 5, wherein the proximal portion of the sleeve has a rounded end.

9. The tampon applicator assembly of claim 2, wherein the plunger mechanism is textured and threaded to mesh with the finger grip portion of the tampon casing so that the plunger mechanism is joined securely with the tampon casing.

10. The tampon applicator assembly of claim 2, wherein the sleeve is elongated so that the sleeve encompasses the tampon applicator section and the plunger section.

11. The tampon applicator assembly of claim 1, wherein said at least one feminine hygiene product comprises two feminine hygiene products disposed in the distal portion of the sleeve.

12. The tampon applicator assembly of claim 11, wherein the two feminine hygiene products are selected from the group consisting of a panty liner, a sanitary napkin, an extra tampon, an absorbent pad, a moistened towelette, a towelette disposal mitt, a simple disposal mitt, a pharmaceutical, a medicinal lotion, a non-medicinal lotion, a lubricant, a cleanser, a spermicidal agent, and an anti-fungal agent.

13. The tampon applicator assembly of claim 1, wherein the partition comprises a rigid material and is rigidly attached to the sleeve.

14. The tampon applicator assembly of claim 1, wherein the partition is integral with the sleeve.

15. The tampon applicator assembly of claim 1, wherein the sleeve is rigid.

16. The tampon applicator assembly of claim 15, wherein the partition is rigid and integral with the sleeve.

* * * * *